United States Patent
Zhang et al.

(10) Patent No.: US 7,494,840 B2
(45) Date of Patent: Feb. 24, 2009

(54) OPTICAL DEVICE WITH IROX NANOSTRUCTURE ELECTRODE NEURAL INTERFACE

(75) Inventors: Fengyan Zhang, Vancouver, WA (US); Sheng Teng Hsu, Camas, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 276 days.

(21) Appl. No.: 11/496,157

(22) Filed: Jul. 31, 2006

(65) Prior Publication Data

US 2009/0011536 A1 Jan. 8, 2009

Related U.S. Application Data (63) Continuation-in-part of application No. 10/971,280, filed on Oct. 21, 2004, now Pat. No. 7,098,144, and a continuation-in-part of application No. 10/971,330, filed on Oct. 21, 2004, now Pat. No. 7,255,745.

(51) Int. Cl.
    *H01L 21/00* (2006.01)
(52) U.S. Cl. .................. 438/85; 438/57; 438/73; 977/904; 977/811; 977/932
(58) Field of Classification Search .............. 438/56, 438/57, 73, 85; 977/904, 811, 932
    See application file for complete search history.

(56) References Cited

U.S. PATENT DOCUMENTS

| 4,628,933 | A | 12/1986 | Michelson | 128/419 R |
|---|---|---|---|---|
| 4,969,468 | A | 11/1990 | Byers et al. | 128/642 |
| 5,109,844 | A | 5/1992 | De Juan et al. | 128/419 R |
| 5,361,760 | A | 11/1994 | Normann et al. | 128/642 |
| 5,865,839 | A | 2/1999 | Doorish | 607/54 |
| 6,298,270 | B1 | 10/2001 | Nisch et al. | 607/54 |
| 6,579,735 | B1* | 6/2003 | Romano et al. | 438/20 |
| 2002/0192441 | A1* | 12/2002 | Kalkan et al. | 428/209 |
| 2003/0042834 | A1* | 3/2003 | Dean et al. | 313/309 |
| 2004/0195957 | A1* | 10/2004 | Hu et al. | 313/495 |
| 2005/0090176 | A1* | 4/2005 | Dean et al. | 445/51 |
| 2007/0210349 | A1* | 9/2007 | Lu et al. | 257/252 |

\* cited by examiner

*Primary Examiner*—Michelle Estrada
*Assistant Examiner*—Jarrett J Stark
(74) *Attorney, Agent, or Firm*—Law Office of Gerald Maliszewski; Gerald Maliszewski (57) ABSTRACT

An optical device with an iridium oxide (IrOx) electrode neural interface, and a corresponding fabrication method are provided. The method provides a substrate and forms a first conductive electrode overlying the substrate. A photovoltaic device having a first electrical interface is connected to the first electrode. A second electrical interface of the photovoltaic device is connected to a second conductive electrode formed overlying the photovoltaic device. An array of neural interface single-crystal IrOx nanostructures are formed overlying the second electrode, where $x \leq 4$. The IrOx nanostructures can be partially coated with an electrical insulator, such as $SiO_2$, SiN, $TiO_2$, or spin on glass (SOG), leaving the IrOx distal ends exposed. In one aspect, a buffer layer is formed overlying the second electrode surface, made from a material such as $LiNbO_3$, $LiTaO_3$, or SA, for the purpose of orienting the growth direction of the IrOx nanostructures.

12 Claims, 5 Drawing Sheets

Fig. 1A

Fig. 1B SUBRETINAL

Fig. 1C EPIRETINAL

OPTICAL DEVICE WITH IROX NANOSTRUCTURE ELECTRODE NEURAL INTERFACE

RELATED APPLICATIONS

This application is a continuation-in-part of a application entitled, IRIDIUM OXIDE NANOTUBES AND METHOD FOR FORMING SAME, invented by Zhang et al., Ser. No. 10/971,280, filed Oct. 21, 2004, now U.S. Pat. No. 7,098,144.

This application is a continuation-in-part of a application entitled, IRIDIUM OXIDE NANOWIRE AND METHOD FOR FORMING SAME, invented by Zhang et al., Ser. No. 10/971,330, filed Oct. 21, 2004, now U.S. Pat. No. 7,255,745.

Both of the above-mentioned applications are incorporated herein by reference.

BACKGROUND OF THE INVENTION

1. Field of the Invention

This invention generally relates to integrated circuit (IC) fabrication and, more particularly, to an optical device with an iridium oxide nanostructure neural interface.

2. Description of the Related Art

Figure 1A:
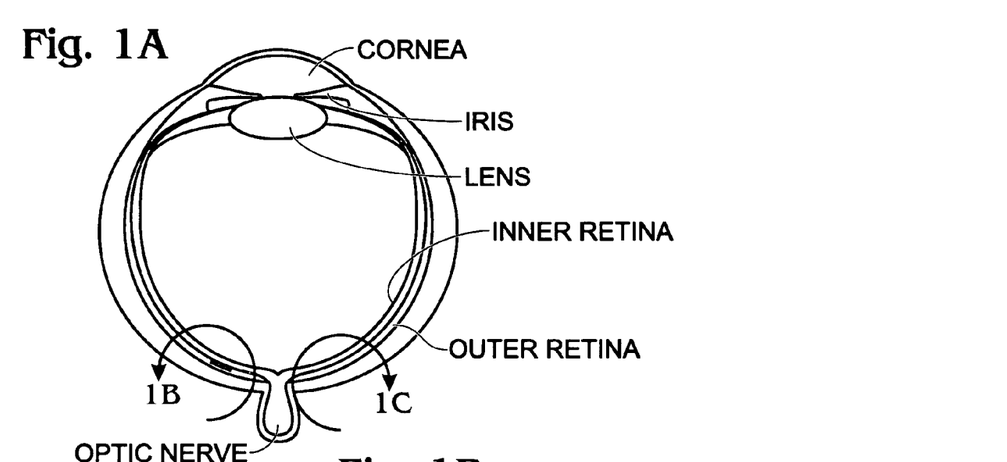
FIGS. 1A through 1C depict the placement of optical electrodes, using epiretinal and subretinal approaches (prior art).
Figures 1B, 1C:
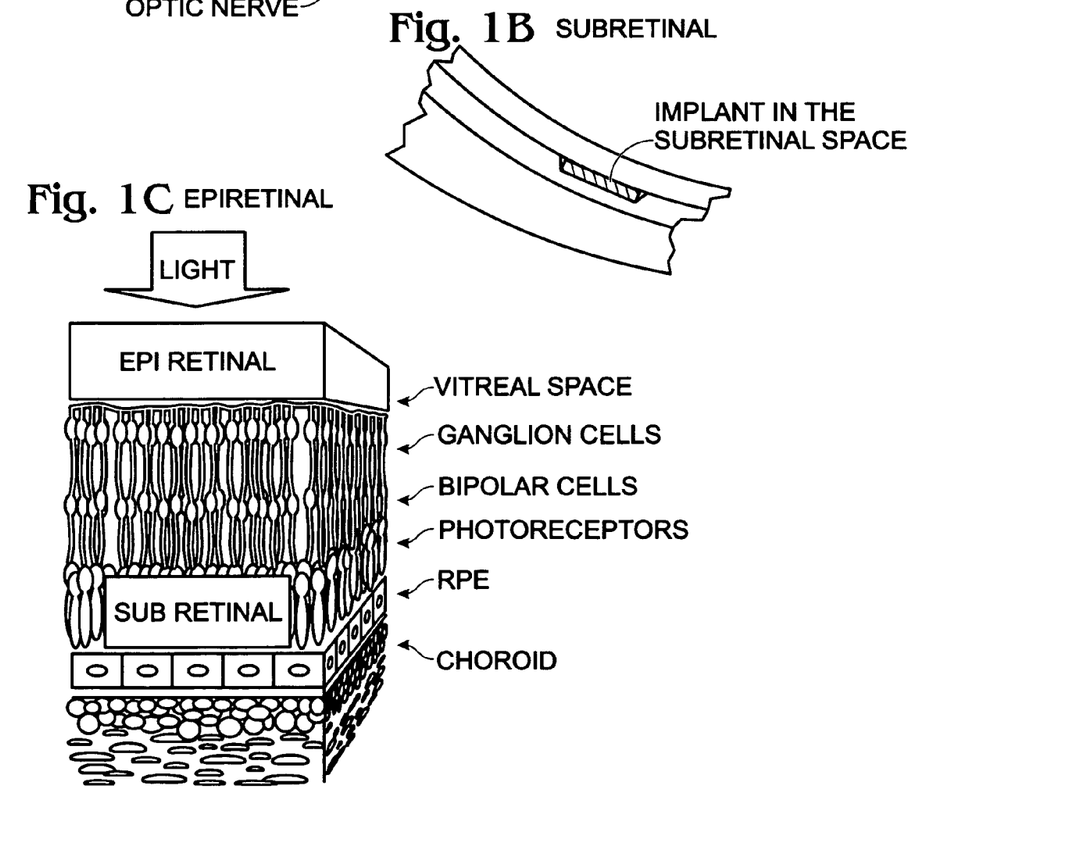

FIGS. 1A through 1C depict the placement of optical electrodes, using epiretinal and subretinal approaches (prior art). Studies show that blind patients with retinitis pigmentosa and masular degeneration can observe a visual percept induced by the direct electrical stimulation of the retina. Recently, retinal prosthesis development has progressed along two directions. The epiretinal approach places electrode in the vitreous fluid, attached to the surface of the retina, while the subretinal approach places electrodes on the outside of retina, wedged between the photoreceptors and the pigment epithelium. FIG. 1C shows the electrode positions for both type of retina prosthesis.

One major difficulty with the epiretinal approach is that the tissue has a very high resistance to electrical stimulation. This high electrical resistance is due to the fact that the retinal is covered by the inner limiting membrane, similar to the blood-brain barrier, and it is impermeable to many types of ions. Since electrical stimulation depends on electrical current building an electrical field across the target nerve cell, a high-resistance barrier in the stimulation pathway prevents current passage. Thus, current is diverted away to other, lower-resistance tissues. To compensate for this loss, the epiretinal approach requires a much larger charge at the electrode surface, to achieve the same stimulation level on the target tissue as a conventionally functioning eye. In human trials, a net charge of ~1 uC (micro-Coulomb) is required for the epiretinal approach, a very high charge for neural stimulation, when compared to 50 nC, which is the level typically required for central nervous system stimulation and subretinal stimulation.

One way to overcome the high-impedance barrier of the epiretinal approach is to penetrate the inner limiting membrane. Arrays of sharp electrodes have been fabricated from silicon and have been used for this purpose. Recently, new techniques promise nano-scale piecing wire electrodes, which can be formed by electrodeposition on a glass substrate contoured to fit the retina.

The subretinal prosthesis avoids the high-impedance barrier problem, by installing electrodes behind the retina. The electrodes are also very close to the bipolar cells, allowing easy (low-charge) stimulation. Low thresholds in the range of 2.8 to 100 $nC/cm^2$ have been reported. However, 178 $uC/cm^2$ is a more realistic number. Subretinal prostheses requires that all components be fitted behind the retina, with the circuits integrated with the electrodes. Power is transferred into the eye via light, which in theory is received by integrated photovoltaic cells, to activate the circuitry. The power output needs to be strictly controlled, since heat dissipation is limited in the subretinal space, and overheating can easily damage the retina.

One technical challenge is the trade-off between electrode density and stimulation charge. Although the total charge injection required to elicit a visual percept is fixed, the maximum charge an electrode can deliver is limited by its surface area. Surpassing this charge density threshold generates undesirable and irreversible electrochemical reactions. In order to elicit a visual percept, the charge density requirement dictates that the electrode must have a total surface area of 1 $mm^2$. When considering the limited area of the retinal implant, this constraint translates into a resolution of 5×5 (25 pixels). However, a visual resolution of at least 25×25 pixels (625 pixels) is desired for recovery of functional sight.

To inject more charge without hydrolysis, an electrode made from a material with a higher injection limit can be used, such as iridium oxide (IrOx). Compared to Pt, an IrOx electrode can inject much more charge for a given voltage swing, by cycling iridium through many oxidation states. Because iridium can exist in many valence states with an insignificant change in atomic size, an iridium electrode can cycle from metallic form (Ir) to higher oxidized form ($IrO_4$) reversibly, allowing it to have a high charge-injection limit of 1 $mC/cm^2$. Using cyclic voltammetry with scan rates of 0.06V/s or slower, a charge injection of >25 $mC/cm^2$ can often be obtained. This behavior is attributed to IrOx porous structure, which requires ionic species to diffuse into deep recessed regions to access the full surface area, as well as due to its many oxidation states, requiring the completion of one state change before proceeding to the next reaction. IrOx is especially ideal for applications with slower stimulation waveforms. For neural stimulation, a current pulse longer than 200 us should be employed. Furthermore, IrOx needs to be biased so that its oxidation state is between Ir3+ and Ir4+ to prevent dissolution that occurs at metallic or higher oxidation states.

A second approach to increase electrode charge-injection is to increase the surface area. The surface area of an electrode is a strong function of its geometry. The area of a solid post electrode can be increased by a factor of 10 easily if it is formed into an array of nanowires/tubes/rods.

Figure 2:
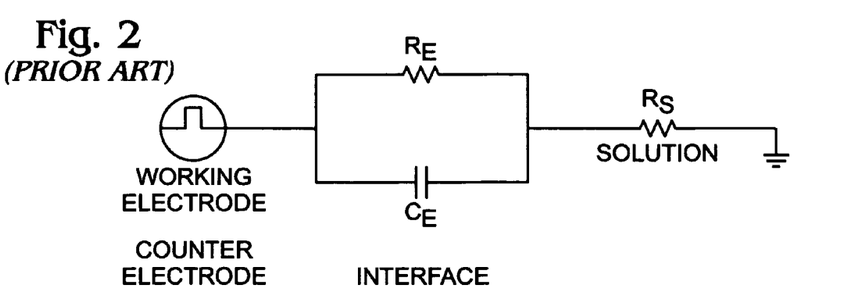
FIG. 2 is a schematic diagram modeling the interface between an electrode and chemically active solution (prior art).

FIG. 2 is a schematic diagram modeling the interface between an electrode and chemically active solution (prior art). Electrodes pass charge mainly through two mechanisms: faradic reactions and capacitive charging. Capacitive charging is the accumulation of charge at the interface between electrons in a metal electrode and ions adjacent to the electrode in a solution, and is represented by $C_E$. A faradic reaction is the transfer of electrons with ions in a solution by a redox reaction of metal species, and is represented by $R_E$. Both the capacitive and faradic components increase linearly with the electrode area because more charge can accumulate at the interface area and be transferred through chemical reactions by increasing the size of the electrode. This larger electrode can be modeled as having a smaller $R_E$ and bigger $C_E$, leading to an increased electrode current at a given potential. Either pulses of constant voltage or current can be used for electrical stimulation. Most frequently, pulses of constant current are used.

Figure 3:
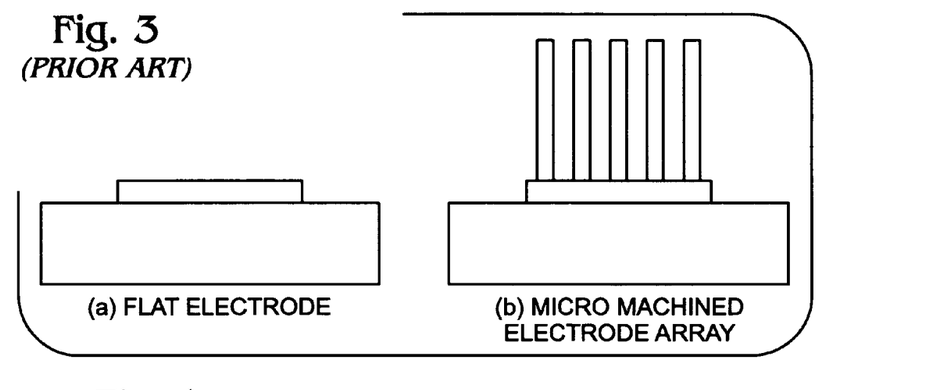
FIG. 3 is a partial cross-sectional view comparing a conventional flat electrode with an electrode array (prior art).

FIG. 3 is a partial cross-sectional view comparing a conventional flat electrode with an electrode array (prior art). Micro-machined neural-stimulating electrode array technology has also been researched. The micro-machined electrode has the advantage of providing additional surface area to decrease the current density, while increasing the electrode density and avoiding material corrosion. However, a key issue to be resolved is the fabrication of an electrode array that can conform to the concave shape of the foveal pit. For example, such as array would need to be formed on a flexible substrate (e.g., polyimide).

Another limitation associated with micromachining technology is size, as the individually machined electrodes cannot be made to a nano-size resolution. Even if a template of nano-sized structures could be micro-machined, plating an array of nanostructures, with a noble metal for example, in a sufficiently high aspect ratio is a big challenge.

Micro-machined electrodes are normally formed from a thick film that is deposited using a physical vapor deposition (PVD) process or electrode plating. In either case, the resultant film, and micro-machined electrode post are also polycrystalline.

Single-crystal $IrO_2$ nanowires/rods/tips have a much longer life than polycrystalline $IrO_2$, due to their higher chemical reaction resistance. Single-crystal IrOx nanostructures also have a higher conductance than polycrystalline $IrO_2$, so they can pass through current more efficiently. However, it is difficult to form single-crystal $IrO_2$ films using conventional PVD or electrode plating methods. $IrO_2$ nanostructures can be formed using a solution method, but these structures have a low mechanical strength and poor crystal quality. Vapor phase transport methods can also be used to form IrO2 nanostructures, but this process requires high substrate temperature, and it is not suitable for use with glass and polyimide substrates.

A technology that can grow free standing highly crystallized nanowires/tubes/rods array of $IrO_x$ on selected areas of electrode would be useful.

It would be advantageous if an optical neural interface could be fabricated using an IrOx nanostructure array formed on a flexible substrate.

It would be advantageous if low substrate temperature chemical vapor deposition (CVD) methods could be used to directly form high-density single-crystal $IrO_2$ nanowires/rods/tip electrode arrays.

SUMMARY OF THE INVENTION

The present invention describes a IrOx nanowires/nanotubes/nanorod array used as a stimulation electrode powered by a photovoltaic device (e.g., a photodiode), which is response to visible light, infrared (IR) light, or both. The IrOx electrode array device has applications as a retinal prosthesis and, more generally, in any medical or biological application requiring a neuron interface to either receive messages from, or deliver messages to the neurons.

Accordingly, a method is provided for forming an optical device with an IrOx electrode neural interface. The method provides a substrate and forms a first conductive electrode overlying the substrate. A photovoltaic device having a first electrical interface is connected to the first electrode. A second electrical interface of the photovoltaic device is connected to a second conductive electrode formed overlying the photovoltaic device. An array of neural interface single-crystal IrOx nanostructures are formed overlying the second electrode, where $x \leq 4$. In one aspect, the IrOx nanostructures have a proximal end attached to the second electrode, and are partially coated with an electrical insulator, such as $SiO_2$, SiN, $TiO_2$, or spin on glass (SOG), leaving the IrOx distal ends exposed.

Rather than micro-machining, the array of IrOx nanostructures can be formed using a chemical vapor deposition (CVD) process to grow IrOx nanostructures from a surface of the second electrode. For example, the CVD process introduces a (methylcyclopentadienyl)(1,5-cyclooctadiene)iridium(I) precursor and uses a metalorganic chemical vapor deposition (MOCVD) process to grow IrOx nanostructures from the second electrode surface. In one aspect, a buffer layer is formed overlying the second electrode surface, made from a material such as LiNbO3, LiTaO3, or SA, for the purpose of orienting the growth direction of the IrOx nanostructures. In another aspect, a growth promotion film is formed over the second electrode, made from a material such as Ti, Co, Ni, Au, Ta, polycrystalline silicon (poly-Si), SiGe, Pt, Ir, TiN, or TaN.

Additional details of the above-described method and an optical device with an IrOx electrode neural interface are presented below.

DETAILED DESCRIPTION

Figure 4:
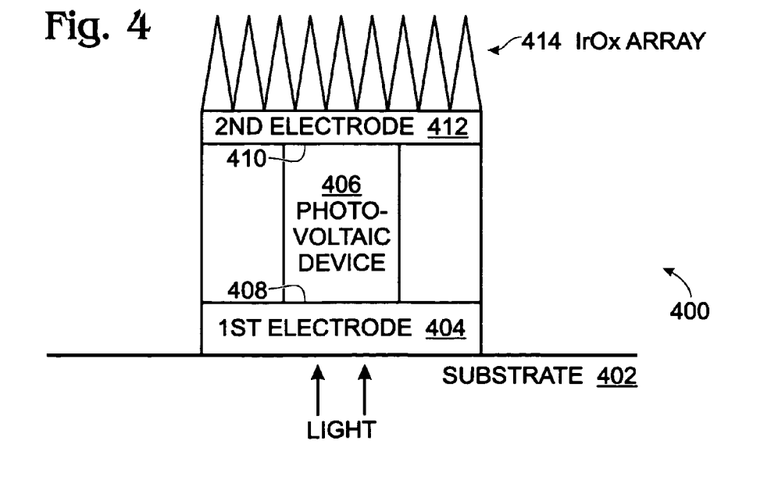
FIG. 4 is a partial cross-sectional view of an optical device with an iridium oxide (IrOx) electrode neural interface.

FIG. 4 is a partial cross-sectional view of an optical device with an iridium oxide (IrOx) electrode neural interface. The device 400 comprises a substrate 402 and a first conductive electrode 404 overlying the substrate 402. The substrate 402 can be a material such as glass, quartz, plastic, or a flexible polyimide. However, the device 400 is not limited to just these exemplary materials.

A photovoltaic device 406 has a first electrical interface 408 connected to the first electrode 404, and a second electrical interface 410. A second conductive electrode 412 overlies the photovoltaic device 406 and is connected to the second electrical interface 410. An array of neural interface single-crystal IrOx ($x \leq 4$) nanostructures 414 overlies the second electrode 412. As used herein, a nanostructure is a structure having nano-sized feature, as defined in more detail below, which may also be referred to as nanowires, nanotubes, nanorods, or the like. Due to the fabrication methods, discussed below, the present invention optical device 400 can uniquely be made from single-crystal IrOx nanostructures having a high aspect ratio, on flexible substrate materials.

A number of photovoltaic devices are available for use in this application. For example, the photovoltaic (PV) device 406 can be a photodiode (not shown) with a pn junction formed in a Si substrate. As shown in FIG. 4, the first electrode 404 is made from a transparent material such as ITO, ZnO, a thin metal layer (e.g. Ag or Au), $SnO_2$:F, or carbon nanotubes. However, the device 400 is not necessarily limited to just these exemplary materials.

Thus, the first electrode 404 passes light to the photovoltaic device 406. The light (wavelength) may be filtered in passing through the first electrode 404, or in the photovoltaic device 406. Using the photodiode example, light can be filtered in response to the thickness of Si substrate separating the pn junction from the first electrode 404. Other examples of photovoltaic devices include conventional Si solar cells, amorphous-Si PIN or NIP structures, dye sensitized solar cells, or other compound semiconductor solar cell structures. However, the present invention optical device 400 is not necessarily limited to any of these exemplary photovoltaic devices 406.

The second electrode 412 is a material such as doped Si, Al, Mo, Ag, TiN, TaN, Pt, Ir, Pd, Ru, or Au. The second electrode 412 need not be transparent. Again, this is a list of exemplary materials, and other conductive electrode materials are well known in the art.

As is well understood in the art, a complete PV device needs to have a conductive electrode connected to each side of a pn (or PIN) junction. The PV device 406 operates by building up voltage or passing a current between the conductive electrodes (404/412). However, the electrode that passes through light must be a transparent conductive electrode (TCO).

The optical device 400 shown in FIG. 4 can be used in epiretinal prosthesis applications. An epiretinal approach would place the IrOx nanostructure array 414 in the vitreous fluid, attached to the surface of the retina. That is, the IrOx nanostructures are pointed toward the retina and light is passing through the opposite side of the device 400.

Figure 5:
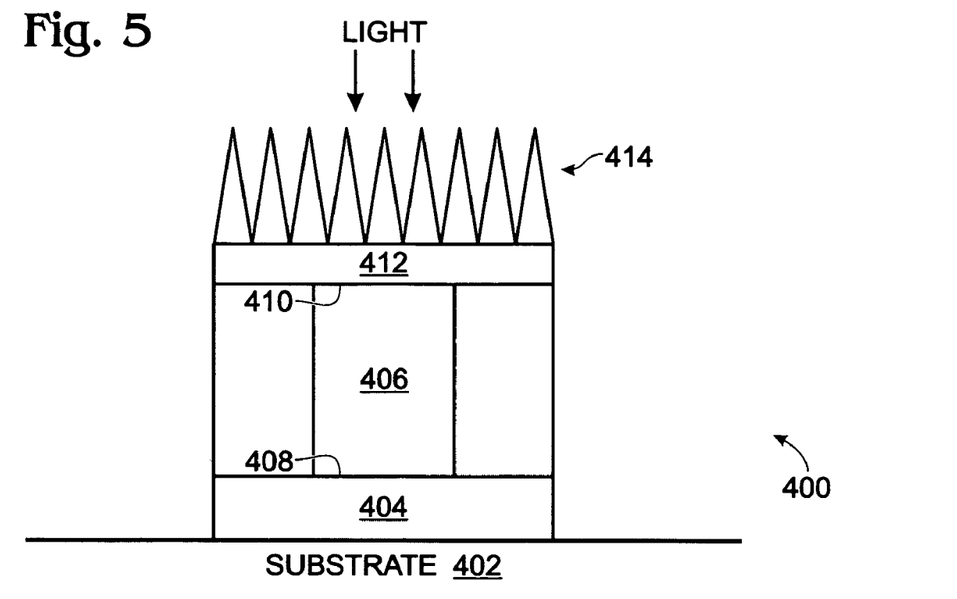
FIG. 5 is a partial cross-sectional view showing a variation of the optical device of FIG. 4.

FIG. 5 is a partial cross-sectional view showing a variation of the optical device of FIG. 4. In this aspect, the second electrode 412 passes light to the photovoltaic device 406, and is made from a transparent material such as ITO, ZnO, a thin metal layer, $SnO_2$:F, or carbon nanotubes. Then, the first electrode 404 can be made from doped Si, Al, Mo, Ag, TiN, TaN, Pt, Ir, Pd, Ru, or Au.

The optical device 400 of FIG. 5 is configured for use in subretinal applications. The electrodes are placed outside of retina, wedged between the photoreceptors and the pigment epithelium. In this case the light will come from the "top" electrode 412, the electrode interfacing with the IrOx nanostructure array 414.

Figure 6:
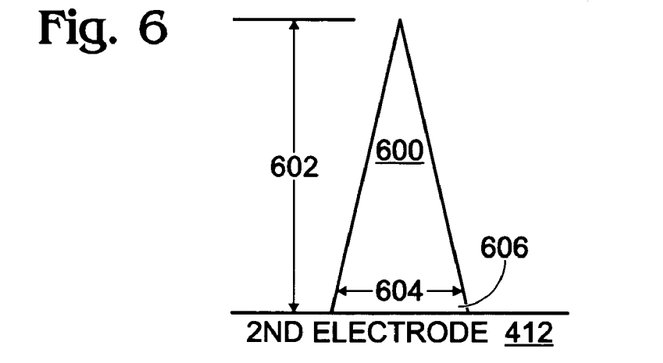
FIG. 6 is a partial cross-sectional view detailing a first aspect of an IrOx nanostructure.

FIG. 6 is a partial cross-sectional view detailing a first aspect of an IrOx nanostructure. The average IrOx nanostructure 600 has an aspect ratio in a range of about 1:1 to about 1:1000. As used herein, aspect ratio is defined as the ratio of the nanostructure height 602, to the nanostructure diameter or width 604 at proximal end 606 (base) attached to the second electrode 412. The IrOx nanostructures have an average height 602 in the range of about 10 nanometers (nm) to about 10 micrometers (μm). The IrOx nanostructures have an average proximal end diameter 604 in a range of about 10 nm to about 10 μm.

Figure 7:
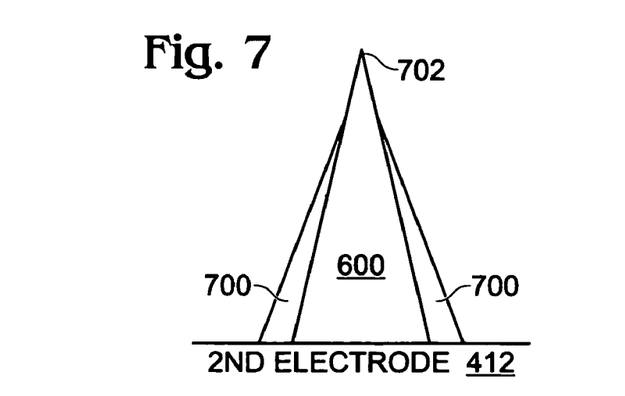
FIG. 7 is a partial cross-sectional view detailing a second aspect of an IrOx nanostructure.

FIG. 7 is a partial cross-sectional view detailing a second aspect of an IrOx nanostructure. In this aspect, an electrical insulator 700 partially coats the IrOx nanostructure 600, leaving the IrOx distal end 702 exposed. The electrical insulator 700 can be a material such as $SiO_2$, SiN, $TiO_2$, or SOG. However, other insulating materials are also known in the art.

Figure 8:
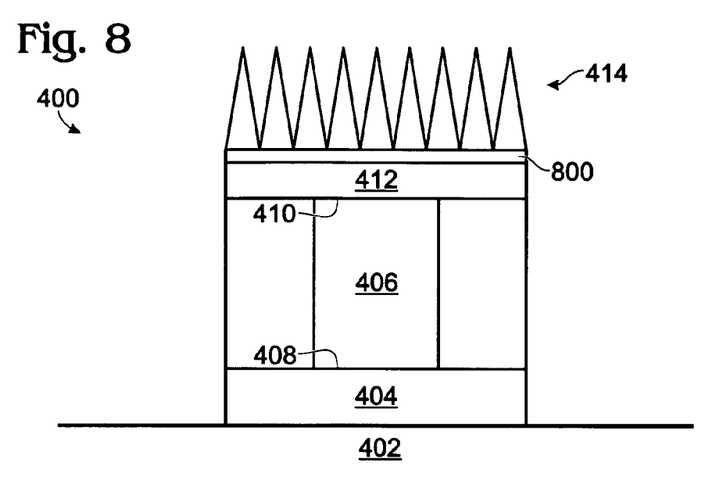
FIG. 8 is a partial cross-sectional view showing a variation of the optical device of FIG. 4 or FIG. 5.

FIG. 8 is a partial cross-sectional view showing a variation of the optical device of FIG. 4 or FIG. 5. In this aspect, a controlled growth buffer layer 800 is interposed between the IrOx nanostructures 414 and the second electrode 412. The buffer layer 800 is made from a material such as LiNbO3 (LNO), LiTaO3 (LTO), or SA, and its use is explained below.

Functional Description

One advantages of using a nanowire/tube/rod array in an optical device is that such as array can provide multiple electrical contacts at the cellular level, for electronically discriminating amongst individual cells or small groups of cells within a tissue or organ. Such an array can direct electrical signals to or from individual cells, or small groups of cells within such tissue or organ, especially neural tissues and organs. Neurologists have long sought electrode devices that can establish stable electrical contact with a large number of individual nerve fibers within a nerve. The ideal electrode device can be adapted to the anatomy of the nerve so that it can penetrate the nerve in a nondestructive fashion, in order to form focused electrical contacts with a very large number of individual nerve fibers. In order to make electrical contact with individual nerve fibers within a nerve, the use of a nanostructure array is a good design choice.

As a biocompatible electrode material, $IrO_x$ has advantages over Au and Pt. Au quickly dissolves when a high potential is applied to it. Pt has the longest history of use as an electrode material and its characteristics are well understood. However, Pt cannot sustain as much reversible faradic charge as IrOx, and it catalyzes water electrolysis at low voltages, limiting its charge-injection capability. Ir is associated with many reversible oxidation states and, thus, has a high faradic current. Further, because it relies heavily on faradic reactions, IrOx is slower in delivering the current.

The $IrO_2$ and IrOx nanostructures been successfully grown on Si, polysilicon, glass, and ITO-coated polyimide flexible substrates, to name a few materials. Selective deposition can be obtained using refractory metal nano-particles, such as Ti, Ni, Au, etc. The growth length, density, and vertical orientation can be controlled by temperature, pressure, flow, substrates and time.

Figure 9A:
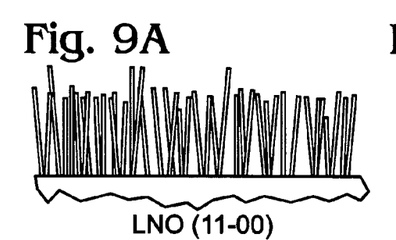
FIGS. 9A and 9B are drawings depicting variations in the orientation of IrOx nanostructures with respect to the surface from which they are grown.
Figure 9B:
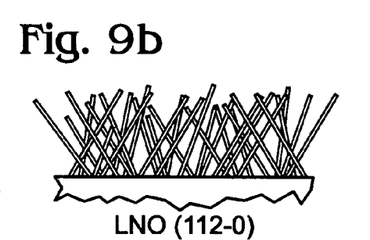

FIGS. 9A and 9B are drawings depicting variations in the orientation of IrOx nanostructures with respect to the surface from which they are grown. In FIG. 9A, the IrOx nanostructure are grown from LNO (11-00), and in FIG. 9B, the growth surface is LNO (112-0). As can be seen from the figures, the orientation of the nanostructures is different. Meaning that the material on which the nanostructures are grown can be used as a growth control variable. $IrO_x$ nanostructures grown on LNO (11-00) are about normal to the wafer surface (within 5°), while $IrO_x$ nanostructures on LNO (112-0) are normal to the wafer surface within about 35° (within 30-40°). Other materials, such as SA and LTO have a similar effect on orienting the nanostructures.

Figure 10:
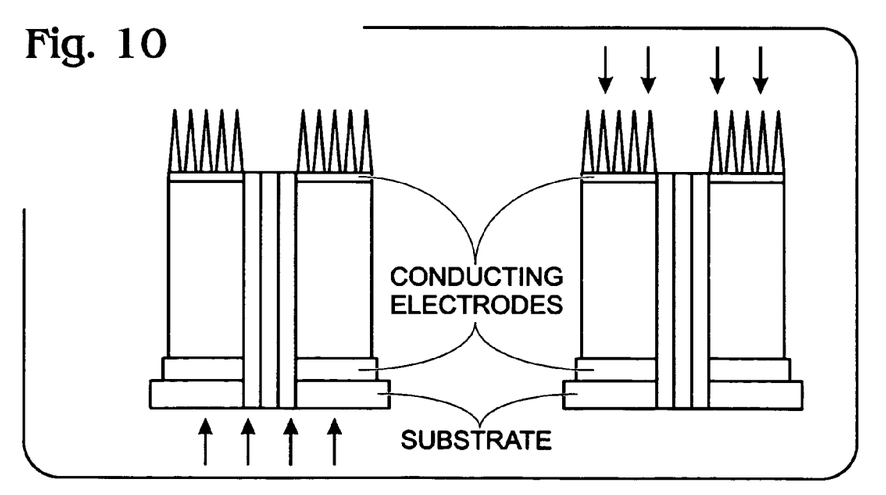
FIG. 10 is a partial cross-sectional view of the optical devices of FIGS. 4 and 5 configured in a device array.

FIG. 10 is a partial cross-sectional view of the optical devices of FIGS. 4 and 5 configured in a device array. $IrO_x$ nanostructures can be selectively deposited on a patterned conducting media, such as Si (doped Si), poly-Si (doped poly-Si), ITO, Ti, TiN, Ta, TaN, Al, Mo, Ag, etc., using CVD methods. The conducting media is connected with one of the electrodes (e.g., the second electrode of FIGS. 4, 5, and 8) of a photovoltaic (photodiode) structure. The photovoltaic structure can be built on a glass or flexible substrate such as polyimide. An array of optical devices is built balancing the need of image resolution against the isolation between individual optical devices needed to prevent the crosstalk. The photovoltaic device can be any state of art technology, such as a conventional Si solar cell, an amorphous-Si PIN or NIP structure, CIGS ($CuIn_{1-x}Ga_xSe_2$) structure, dye sensitized solar cell, or other compound semiconductor solar cell structures. Multi-junction cells can be used to increase the efficiency and obtain wider spectrum responses. Both vertical and lateral photovoltaic structure can also be used. Between the cells, holes can be drilled to let the nutrition pass through the electrode structure.

As noted above, the $IrO_x$ nanostructures can also be coated with an insulating media, using spin on methods for example, to enhance the strength of the electrode array. This insulating layer has a thickness sufficient to just cover, or expose the electrode tips for stimulating the bio tissue. Either a direct light energy source or an indirect light energy source (such as from LED) can be used to activate the photovoltaic arrays.

Figure 11:
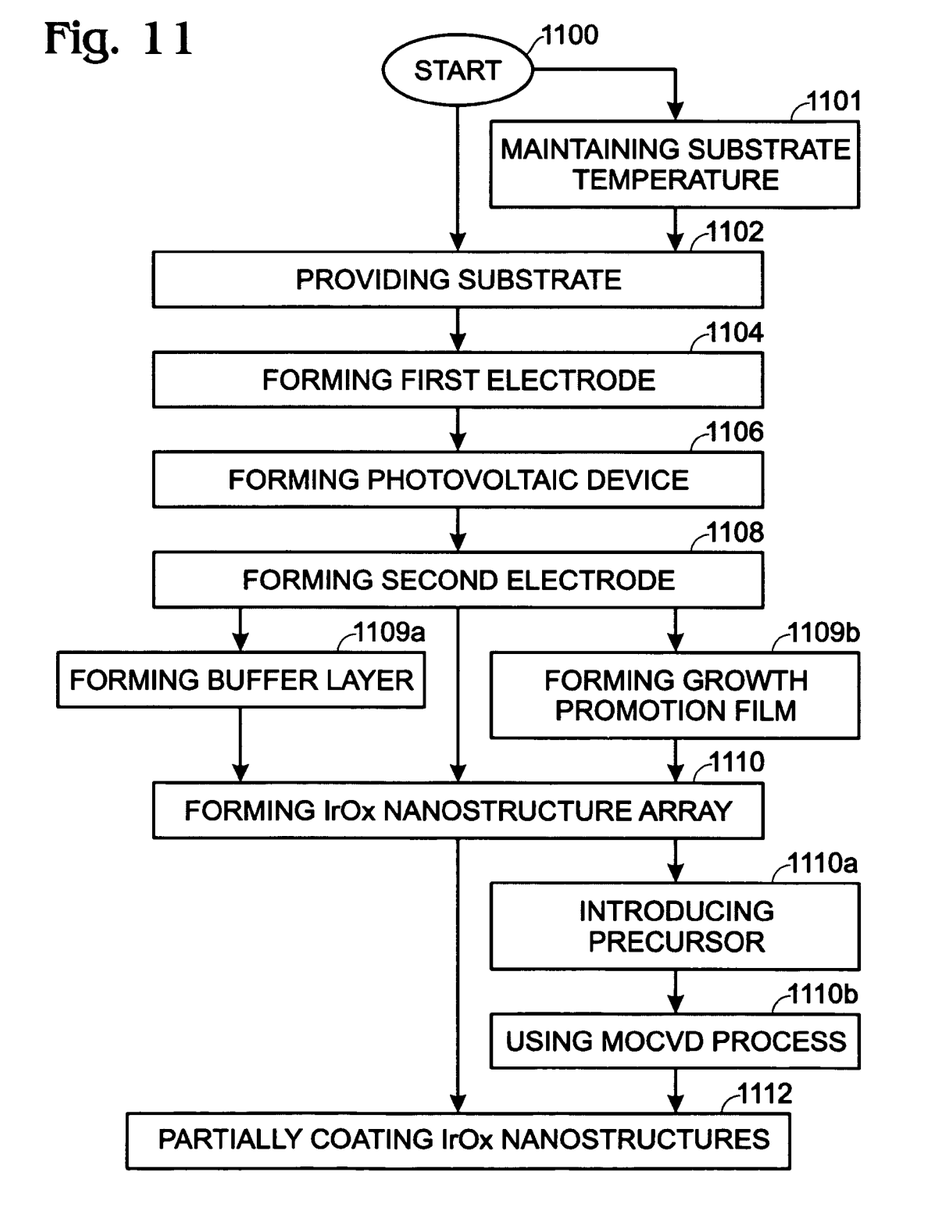
FIG. 11 is a flowchart illustrating a method for forming an optical device with an IrOx electrode neural interface.

FIG. 11 is a flowchart illustrating a method for forming an optical device with an IrOx electrode neural interface. Although the method is depicted as a sequence of numbered steps for clarity, the numbering does not necessarily dictate the order of the steps. It should be understood that some of these steps may be skipped, performed in parallel, or performed without the requirement of maintaining a strict order of sequence. The method starts at Step 1100.

Step 1102 provides a substrate. Step 1104 forms a first conductive electrode overlying the substrate. Step 1106 forms a photovoltaic device having a first electrical interface connected to the first electrode, and a second electrical interface. Step 1108 forms a second conductive electrode overlying the photovoltaic device connected to the second electrical interface. Step 1110 forms an array of neural interface single-crystal IrOx nanostructures overlying the second electrode, where $x \leq 4$. As noted above, the IrOx nanostructures have an average aspect ratio in a range of about 1:1 to about 1:1000.

In one aspect, Step 1110 forms IrOx nanostructures with a proximal end attached to the second electrode, and a distal end. Then, Step 1112 forms an electrical insulator partially coating the IrOx nanostructures, leaving the IrOx distal ends exposed. For example, the electrical insulator includes partially coating the IrOx nanostructures can be $SiO_2$, SiN, $TiO_2$, or SOG.

In another aspect, forming the array of IrOx nanostructures in Step 1110 includes using a CVD process to grow IrOx nanostructures from a surface of the second electrode. For example, using a CVD process to grow IrOx nanostructures in Step 1110 may include substeps. Step 1110a introduces a (methylcyclopentadienyl)(1,5-cyclooctadiene)iridium(I) precursor, and Step 1110b uses a metalorganic chemical vapor deposition (MOCVD) process to grow IrOx nanostructures from the second electrode surface. More explicitly, introducing the (methylcyclopentadienyl)(1,5-cyclooctadiene)iridium(I) precursor in Step 1110a may include additional substeps (not shown). Step 1110a1 initially heats the precursor to a first temperature in the range of 60 to 90 degrees C. Step 1110a2 maintains the first temperature in the transport line introducing the precursor. Step 1110a3 mixes the precursor with a carrier gas, and Step 1110a4 establishes a final pressure in the range of 1 to 50 Torr. Additional details of the fabrication process can be found in the parent applications listed above in the "Related Applications" Section.

In another aspect, Step 1109a forms a buffer layer overlying the second electrode surface, made from a material such as LiNbO3, LiTaO3, and SA. Then, forming the array of IrOx nanostructures in Step 1110 includes orienting the growth direction of the IrOx nanostructures with respect to the second electrode surface, in response to forming the buffer layer.

In a different aspect, Step 1101 establishes a substrate temperature in the range of 200 to 600 degrees C. Step 1109b forms a growth promotion film with non-continuous surfaces overlying the second electrode surface. Then, Step 1110b uses the MOCVD process to grow IrOx nanostructures from the growth promotion film surfaces. Typically, the growth promotion film used in Step 1109b has a thickness in the range of 0.5 to 5 nanometers (nm). The growth promotion film material can be Ti, Co, Ni, Au, Ta, polycrystalline silicon (poly-Si), SiGe, Pt, Ir, TiN, and TaN.

An optical device with an IrOx electrode neural interface, and corresponding fabrication processes have been provided. Examples of specific materials, process steps, and structures have been presented to illustrate the invention. However, the invention is not limited to merely these examples. Other variations and embodiments of the invention will occur to those skilled in the art.

We claim:

1. A method for forming an optical device with an iridium oxide (IrOx) electrode neural interface, the method comprising:
   providing a substrate;
   forming a first conductive electrode overlying the substrate;
   forming a photovoltaic device having a first electrical interface connected to the first electrode, and a second electrical interface;
   forming a second conductive electrode overlying the photovoltaic device connected to the second electrical interface; and,
   forming an array of neural interface single-crystal IrOx nanostructures overlying the second electrode, where $x \leq 4$.

2. The method of claim 1 wherein forming the array of IrOx nanostructures includes forming IrOx nanostructures with a proximal end attached to the second electrode, and a distal end; and,
   the method further comprising:
   forming an electrical insulator partially coating the IrOx nanostructures, leaving the IrOx distal ends exposed.

3. The method of claim 2 wherein forming the electrical insulator includes partially coating the IrOx nanostructures with a material selected from a group consisting of SiO2, SiN, TiO2, and spin on glass (SOG).

4. The method of claim 1 wherein forming the array of IrOx nanostructures includes using a chemical vapor deposition (CVD) process to grow IrOx nanostructures from a surface of the second electrode.

5. The method of claim 4 further comprising:
   forming a buffer layer overlying the second electrode surface; and,
   wherein forming the array of IrOx nanostructures includes orienting the growth direction of the IrOx nanostructures with respect to the second electrode surface, in response to forming the buffer layer.

6. The method of claim 5 wherein forming the buffer layer includes forming a buffer layer from a material selected from a group consisting of LiNbO3, LiTaO3, and SA.

7. The method of claim 4 wherein using a CVD process to grow IrOx nanostructures from the surface of the second electrode includes:
   introducing a (methylcyclopentadienyl)(1,5-cyclooctadiene)iridium(I) precursor; and using a metalorganic chemical vapor deposition (MOCVD) process, growing IrOx nanostructures from the second electrode surface.

8. The method of claim 7 wherein introducing the (methylcyclopentadienyl)(1,5-cyclooctadiene)iridium(I) precursor includes:
 initially heating the precursor to a first temperature in the range of 60 to 90 degrees C.;
 maintaining the first temperature in the transport line introducing the precursor;
 mixing the precursor with a carrier gas; and,
 establishing a final pressure in the range of 1 to 50 Torr.

9. The method of claim 1 further comprising:
 establishing a substrate temperature in the range of 200 to 600 degrees C.
 forming a growth promotion film with non-continuous surfaces overlying the second electrode surface;
 wherein forming an array of IrOx nanostructures includes:
  introducing a (methylcyclopentadienyl)(1,5-cyclooctadiene)iridium(I) precursor; and
  using a MOCVD process, growing IrOx nanostructures from the growth promotion film surfaces.

10. The method of claim 9 wherein forming the growth promotion film includes forming a growth promotion film having a thickness in the range of 0.5 to 5 nanometers (nm).

11. The method of claim 9 wherein forming the growth promotion film includes forming a growth promotion film material selected from the group including Ti, Co, Ni, Au, Ta, polycrystalline silicon (poly-Si), SiGe, Pt, Ir, TiN, and TaN.

12. The method of claim 1 wherein forming the array of IrOx nanostructures includes forming IrOx nanostructures, having an average aspect ratio in a range of about 1:1 to about 1:1000.

* * * * *